United States Patent [19]

Mahjour et al.

[11] Patent Number: 5,019,395

[45] Date of Patent: May 28, 1991

[54] COMPOSITIONS WITH ENHANCED PENETRATION

[75] Inventors: Majid Mahjour, Netcong; Bernadette Mauser, Lyndhurst; Zahra Rashidbaigi, Morris Plains; Edwards E. Linn, Wanaque, all of N.J.

[73] Assignee: Warner-Lambert Company, Morris Plains, N.J.

[21] Appl. No.: 391,808

[22] Filed: Aug. 9, 1989

Related U.S. Application Data

[63] Continuation-in-part of Ser. No. 165,322, Mar. 8, 1988, abandoned.

[51] Int. Cl.$^5$ .............................................. A61F 13/00
[52] U.S. Cl. ...................................... 424/449; 424/447; 424/448; 424/434; 514/946; 514/470; 514/266; 514/620
[58] Field of Search ............... 424/447, 448, 449, 434; 514/946 VR, 470, 266, 620; 554/317

[56] References Cited

U.S. PATENT DOCUMENTS

| | | | |
|---|---|---|---|
| 3,551,554 | 12/1970 | Herschler | 424/154 X |
| 4,336,243 | 6/1982 | Sanvordeker et al. | 424/449 |
| 4,440,777 | 4/1984 | Zupan | 514/946 X |
| 4,611,008 | 9/1986 | Heinzelmann | 514/470 |
| 4,816,456 | 3/1989 | Summers | 514/252 |
| 4,840,796 | 6/1989 | Sweet et al. | 424/448 |
| 4,883,669 | 11/1989 | Chien et al. | 424/449 |

FOREIGN PATENT DOCUMENTS 2107588  10/1982  United Kingdom ................... 31/45

OTHER PUBLICATIONS

EP Search Report.
Physicians Desk Reference (PDR), 26th Ed., 1972, p. 105.
Summers et al, "Oral Tetrahydroaminoacridine in Long-Term Treatment of Senile Dementia, Alzheimer Type", The New England J. of Med., Nov. 13, 1986, vol. 315, No. 20, pp. 1241–1245.

*Primary Examiner*—Thurman Page
*Assistant Examiner*—Leon R. Horne
*Attorney, Agent, or Firm*—Elizabeth M. Anderson

[57] ABSTRACT

Penetration of various drugs through living membranes is improved by their use in transdermal compositions containing certain penetration-enhancing systems. A new delivery device is also described.

23 Claims, No Drawings

COMPOSITIONS WITH ENHANCED PENETRATION

CROSS-REFERENCE

This application is a continuation-in-part of pending application Ser. No. 165,322, filed Mar. 8, 1988, now abandoned.

BACKGROUND OF THE INVENTION

Diphenhydramine, hydrochloride (Benadryl®, or 2-(diphenylmethoxy) N, N-dimethylethylamine), is known to be useful for its antihistaminic, anticholinergic, antitussive, antiemetic, and sedative properties The compound and its preparation are described in U.S. Pat. No. 2,421,714 which is hereby incorporated by reference.

The base is a liquid and its salts have acceptable solubilities in standard liquid media. Thus, diphenhydramine-based drugs are conventionally used in dosage forms such as oral and parenteral. However, there are undesirable digestive side effects possible with oral formulations. Generally there are compliance problems with parenterals.

Diphenhydramine is a nonprescription drug widely used alone or in combination with other drugs as an effective antihistamine with a sedative side effect. Carruthers, et al (Clin Pharmacol Ther 1978; 23:375–382) showed that the sedative side effect of diphenhydramine hydrochloride could be eliminated if the blood concentration remains in the range of 25 to 50 ng/ml (equivalent to 21.9 to 43.9 ng/ml diphenhydramine base). This indicates that a sustained dosage form which could provide such constant blood levels would be a very useful and viable dosage form in the treatment of allergy.

Tetrahydroaminoacridine (1,2,3,4-tetrahydro-9-acridinamine, tacrine, or THA) is a very old compound known to have anticholinesterase activity. It has been shown that THA improves the amnesia characteristic of Alzheimer's disease (Brinkman and Gershon, 1983; Flood et al, 1985; Rathman and Conner, 1984; McGeer, 1984).

Tazifylline is known to be useful as an antihistamine. It is covered in U.S. Pat. No. 4,374,835 which is hereby incorporated by reference.

Atenolol, 4-[2-hydroxy-3-[(1-methylethyl)amino]-propoxy]benzeneacetamide, is covered in U.S. Pat. Nos. 3,663,607 and 3,836,671 hereby incorporated by reference. It is a β-adrenergic blocker.

2-Methoxy-4-[2-(5-methyl-1H-pyrazol-3-yl)ethenyl]-phenol is covered in pending application 861,179. It has antiasthma, antiallergy, antiinflammatory, antipsoriatic, analgesic, and cardiovascular activities.

Diltiazem and verapamil are coronary vasodilators (calcium antagonists) covered by U.S. Pat. Nos. 3,562,257 and 3,261,859.

Hydrocortisone is an adrenocortical steroid and is useful as a topical antiinflammatory. Hydrocortisone and methods for preparing it are covered in U.S. Pat. No. 2,602,769.

While the above drugs are highly efficacious, their use is subject to such problems as dose dumping and high drug use requirements.

U.S. Pat. No. 4,611,008 discloses the use of Miglyol-812 or Miglyol-829 in a coronary-active gel-containing preparation.

U.S. Pat. No. 4,331,651 covers in part, caprylic/capric acid -1,2-propanediol diester used as a release-promoting substance used in a silicone rubber carrier for an active ingredient.

U.S. Pat. No. 4,336,243 covers a microsealed transdermal delivery pad for nitroglycerin administration which contains a silicon matrix having microsealed compartments of silicone rubber mixed with a hydrophilic solvent system, the solvent system can contain a saturated coconut oil such as miglyol oil which improves the transport and absorption of the nitroglycerin.

U.S. Pat. No. 4,788,063 covers a transdermal pharmaceutical composition for delivery of cholinergic and anticholinergic basic drugs. The active ingredients are in a vehicle such as a lower fatty acid which serves as a solvent and a transdermal delivery agent.

U.S. Pat. No. 4,485,087 covers a process for preparing a composite pharmaceutical preparation.

European Application 243891 covers a laminar structure for administering a chemical at a controlled rate.

SUMMARY OF THE INVENTION

It has been discovered that therapeutically active agents such as diphenhydramine, tetrahydroaminoacridine (THA), atenolol, tazifylline, 2-methoxy-4-[2-(5-methyl-1H-pyrazol-3-yl)ethenyl]phenol, diltiazem, verapamil, sex hormones such as estradiol or progesterone or a mixture thereof, corticosteroids such as hydrocortisone and the like in combination with a solvent, Miglyol® oil with or without a gelling agent such as Aerosil® 200 provide a higher flux value than formulations without Miglyol® oil when applied on skin. Excipients known to one skilled in the art are included. Other known enhancers may be added such as fatty acid.

Gastrointestinal problems associated with some drugs which are administered orally are thus eliminated. The gradual release of a drug via a membranal tissue minimizes the risk of dose dumping and other side effects.

In addition, the use of the present invention results in a reduction in overall drug load dose. Furthermore, a patch or other transmembranal device serves as a reminder to the patient to administer the proper dosage.

Moreover, the present invention provides a permeation enhancer which is nonirritating to skin.

These and other advantages of the invention will become apparent upon consideration of the following description of the invention.

A preferred embodiment of the instant invention comprises a transmembranally administrable composition of a therapeutically effective amount of a medicament and Miglyol® 840 with ethanol in a penetration enhancing effective amount.

In another preferred embodiment of the instant invention, a transmembranal composition of diphenhydramine or a pharmaceutically acceptable salt thereof is combined with Miglyol®, with or without a gelling agent, and an alcohol in the form of a gel. The gel would be covered by a controlling or a noncontrolling membrane compatible with manufacturing processes and capable of providing the desired flux of the active ingredient. Microporous membranes, Silastic® membranes, and/or polyurethane (with polyester or polyether backbone) membranes among other appropriate transdermal devices may be used.

The side effects often associated with the use of diphenhydramine in oral and parenteral formulations can be overcome by administration of the drug via application to body membranes for absorption into the system.

In still another preferred embodiment of the instant invention, a transmembranal composition of tetrahydroaminoacidine or a pharmaceutically acceptable salt thereof is combined with Miglyol ® 840 and ethanol with or without a gelling agent.

The side effects associated with high doses of THA orally administered of some liver toxicity are reduced using the instant invention.

Transdermal delivery systems are not always efficacious due to such factors as the failure of the drug to sufficiently penetrate the cutaneous membrane and enter the body to produce systemic therapeutic effects. The present invention uses a novel penetration enhancer to deliver efficacious amounts of the desired drug to the body. The compositions and methods of the instant invention have several advantages over conventional systems for the delivery of drugs. One principal advantage concerns the undesirable side effects associated with administration via dosage forms which are swallowed or injected. For instance, the nausea and/or other gastrointestinal discomfort associated with liquids and solids which are swallowed is eliminated when transmembrane administration is employed. The compositions of the instant invention are introduced into the body via various membranes, for example, transdermally, buccally, rectally, and nasally.

Also, the storage and transportation problems associated with liquid dosage forms are generally eliminated when transmembrane administration is employed. These are usually creams, gels, and solid suppositories. In the compositions of the instant invention the transdermal delivery of the drugs has several advantages. One such is the gradual release of the drug via membranal tissue, for example, on the skin or in the nasal passages, minimizes the risk of dose dumping and can also reduce the overall drug loading dose. Also, a patch or other transdermal device serves as a reminder to the patient to administer the proper dosage of the drug.

In addition the instant invention covers a carrier of drugs, a new delivery device, which is a dual-ply laminate of a silicone elastomer and a macroporous polyethylene slab. This is especially useful for transdermal delivery of drugs that require a large maintenance dose.

These and other advantages of the invention will be apparent upon the following description of the invention.

DETAILED DESCRIPTION

The present invention concerns a composition for penetration enhancement, i.e., for use in transmembranal administration of drugs. Such a composition comprises (a) about 0.1% to about 8% by weight of one or more drugs selected from the group consisting of diphenhydramine, tetrahydroaminoacridine, atenolol, tazifylline, 2-methoxy-4-[2-(5-methyl-1H-pyrazol-3-yl)ethenyl]phenol, diltiazem, verapamil, sex hormones such as estradiol or progesterone or a mixture thereof, hydrocortisone and the like and the pharmaceutically acceptable salts thereof, (b) about 0% to about 99.8% by weight of a solvent, (c) about 0% to about 15% by weight of a gelling agent and other excipients or diluents as would occur to one skilled in the art.

Preferably a composition comprises
(a) about 0.2% to about 8% of a therapeutically active medicament,
(b) about 0.1% to about 80% of Miglyol ® 840 and alcohol, and
(c) about 0.5% to about 12% of gelling agent.

All percentages recited herein are weight percentages based on total composition weight unless otherwise specified.

Also preferably a composition comprises a composition according to claim 1 comprising:
(a) about 0.2% to about 8% of a therapeutically active medicament, and
(b) about 0.1% to about 80% of Miglyol ® 840 and alcohol.

The term diphenhydramine and pharmaceutically acceptable salts thereof is intended to include all forms of diphenhydramine and/or its analogs which have medical utility. Thus, diphenhydramine, its hydrochloride salt, and the like are contemplated. Mixtures may also be used.

The use of a diphenhydramine-based drug is but one example of a transmembranal formulation of the instant invention. The use of tetrahydroaminoacridine, atenolol, tazifylline, 2-methoxy-4-[2-(5-methyl-1H-pyrazol-3-yl)ethyl]phenol, diltiazem, verapamil, sex hormones, and hydrocortisone are also examples. The use of other beneficial substances is also contemplated. Thus sedatives, tranquilizers, antiinfectives, cardiotonics, cognition activators, and the like may be included in the compositions of the invention.

Generally the drug component will comprise about 0.1% to about 50%, preferably about 0.2% to about 30%, more preferably about 0.2% to about 5% by weight of the total composition.

Other components such as alcohol and a gelling agent are also contemplated. A preferred gelling agent is Aerosil ® 200 (B.F. Goodrich, silicone oxide). The gelling agent will comprise from about 0% to about 15% by weight of the total composition. Preferred is from about 0.5% to about 12%. All acceptable excipients, antioxidants, preservatives, including Wickenol ® 535 (Wickhen Product Inc., a mixture of mono- or di-triglyceride of wheat germ oil) and Vit. E as included in the instant invention.

A controlling membrane is also contemplated. Preferred membranes include microprous membranes, Silastic ® membrane, polyurethane membranes, and the like.

A method of administering the above composition includes (a) contacting the drug with a vehicle to produce a transmembranal formulation and (b) applying that formulation in a suitable device to body membrane for absorption therethrough.

Other conventional adjuncts, for example, colorants, perfumes, stabilizers, and the like can also be employed in compositions of the present invention.

The permeation-enhancing portion of the instant invention is a substance which functions to assist in the migration of the drug component(s) through the membranes and into the bloodstream. Thus, any agent(s) which function to hasten and/or to regulate the transmembranal passage or systemic release of drug(s) can be used in combination with Miglyol ® 840.

Generally the solvent, the permeation-enhancing component, will comprise about 0.1 to 99.9%, preferably to 80%, and most preferably 50 to 80% by weight of the total composition. The active ingredient permeates through the skin as a neat drug (base) or in formulations containing a solvent.

The solvent component will comprise at least one solvent for the drug component. Useful solvents include but are not limited to Miglyol® oils, alcohol, IPM (isopropylmyristate), and the like. Mixtures of two or more are also usable. Preferably the solvent is Miglyol® 840. Still more preferable is a Miglyol® 840:ethanol in a ratio of from 0% to 90% to 90% to 0%. The solvent component will comprise about 0.1, to about 99.8%, preferably about 50 to about 80% and most preferably from about 50 to about 70% by weight of the total composition.

The term solvent is intended to include that portion of the formulation which provides the flux of the active ingredient. The preferred solvent is Miglyol® 840 which is a propylene glycol di-ester of caprylic and capric acids from coconut oil. (Available from Dynamit Nobel Chemicals.)

The Miglyol® 840 and an alcohol, preferably ethanol, provides an excellent permeation enhancing system.

Table VI below shows the effect of ethanol, Miglyol® 840, and ethanol:Miglyol® 840 binary solvent system on the permeation of various compounds across hairless mouse skin.

The following example illustrates one embodiment of the invention. It is not intended to limit the scope of the invention in any way.

The drug-containing gel composition:

| Ingredients | Percent (%) w/w |
|---|---|
| Diphenhydramine Base | 20.0 |
| Miglyol® 840 | 73.0 |
| Wickenol® 535 | 0.5 |
| Vit. E Alcohol USP | 0.05 |
| Aerosil® 200 | 6.45 |

Both Silastic® membrane and polyurethane membranes (with polyester or polyether backbone) were evaluated. In addition the effect of the gelling agent Aerosil® 200 on diphenhydramine flux was determined.

Pharmaceutical compositions containing Miglyol® neutral oils are useful in effecting transdermal delivery of a therapeutic dose of an active drug to the system of mammals. Tables I-VI below show a series of comparative in vitro diffusion studies illustrating the usefulness of Miglyol® oils, e.g., Miglyol® 840 (Dynamit Nobel Chemicals) as effectively enhancing the penetration of differeng drugs across biological membranes. Hairless mouse skin was used.

The in vitro permeation of compounds: atenolol, diltiazem, hydrocortisone, tazifylline, THA, and verapamil from a binary solvent system composed of ethanol and Miglyol® Oil 840, as well as from the xindividual components across hairless mouse skin was evaluated. As Table VI indicates, the solvent mixture significantly improved the average flux values (calculated by averaging the flux values obtained at each sampling time) of all the compounds within a 24-hour time period in comparison to that of ethanol or Miglyol Oil alone. The enhancement effect was most profound on tazifylline and hydrocortisone permeation. Minimal enhancement effect was observed on the permeation of verapamil from the binary solvent system, as compared to that of Miglyol Oil alone; while an enhancement factor of 4.76 was obtained in comparison to ethanol.

Table I shows a comparison of Miglyol® 840 on the permeation of tazifylline with other skin permeation enhancers across hairless mouse skin. The Miglyol® 840 shows the highest flux value.

The effect of varying the ethanol to Miglyol Oil ratio on the permeation of diltiazem was also studied. As shown in Table II, increasing the alcohol concentration in the formulation from 10 to 30% improved the flux value threefold.

These data indicate that Miglyol Oil 840 significantly improved the permeation of the model compounds, and the ethanol:Miglyol Oil mixture is superior to the individual component of the solvent system.

TABLE I

Comparison of Miglycol® 840's Effect on the Permeation of Tazifylline with Other Skin Permeation Enhancers Across Hairless Mouse Skin

| Formulation | Donor Conc.* (mg/ml) | Flux ($\mu g/cm^2/h$) | Lag Time (h) | Permeability (cm/sec) × $10^7$ |
|---|---|---|---|---|
| LA:PG 10:90 | 6.54 | 20.48 | 1.2 | 8.70 |
| LA:Miglyol® 840 10:90 | 14.37 | 33.68 | 8.47 | 6.51 |
| DMSO:$H_2O$ 80:20 | 5.96 | 25.08 | 15.97 | 11.69 |
| ETOH:Miglyol® 840 20:80 | 52.13 | 290.58 | 0.77 | 15.48 |
| LA:PG:TA 20:30:50 | 46.07 | 104.66 | 8.01 | 6.31 |
| Miglyol®-Gel: Miglyol® 840:ETOH 66.6:26.7:6.7 | 15.08 | 37.33 | 3.23 | 6.88 |
| DPH:PG 50:50 | 16.3 | 7.81 | 10.45 | 1.33 |

*saturated solution
A steady state flux value
  Estimated by dividing flux value by initial drug concentration
LA = Linoleic Acid
PG = Propylene Glycol
DMSO = Dimethyl Sulfoxide
TA = Triacetin
ETOH = Ethanol
DPH = Diphenhydramine

TABLE II

Effect of Miglyol ® 840 on Diphenhydramine (DPH) Flux Value Across Hairless Mouse Skin

| Formulation w/w | Flux ($\mu$g/cm$^2$/h) | Lag Time (h) |
|---|---|---|
| 60:40 Miglyol ® 840:DPH | 132 ± 21 | 0 |
| 70:30 Miglyol ® 840:DPH | 118 ± 9 | 0 |
| 90:10 Miglyol ® 840:DPH | 103 ± 18 | 0.2 ± 0.2 |
| 95:5 Miglyol ® 840:DPH | 70 ± 19 | 0.3 ± 0.2 |
| Neat DPH | 94 | 0 |

A steady state flux value

TABLE III

Effect of Miglyol ® 840 on Enhancing the Penetration of 2-Methoxy-4-[2-(5-methyl-1H-pyrazol-3-yl)ethenyl]phenol Across Hairless Mouse Skin

| Solvent System | Drug Conc. (mg/ml) | Flux Value ($\mu$g/cm$^2$/h) | Lag Time (h) |
|---|---|---|---|
| Acetone | 5 | 6.46 ± 2.43 | 1.68 ± 0.67 |
| LA:PG:TA 20:30:50 w/w | 20 | 7.1 ± 5.8 | 2.65 ± 0.16 |
| Miglyol ® 840:ETOH 80:20 w/w | 10 | 41.33 ± 7.68 | 2.2 ± 0.1 |

A steady state flux value

TABLE IV

Skin Penetration Enhancement Effect of Miglyol ® 840 on THA as Compared with Other Penetration Enhancers

| Solvent System | Drug Conc. % | Flux Value ($\mu$g/cm$^2$/h) | Lag Time (h) |
|---|---|---|---|
| LA:PG:TA 20:30:50 w/w | 2 | 168.6 ± 1.9 | 2.9 ± 1.3 |
| LA:ETOH:H$_2$O 5:70:25 w/w | 4 | 645.6 ± 87 | 6.5 ± 0.5 |
| DPH:PG 50:50 w/w | 4 | 102.45 ± 5.5 | 5.1 ± 0.56 |
| Miglyol ® 840:ETOH 80:20 | 4 | 2011.5 ± 117 | 1.3 ± 0.2 |
| PG | 4 | 106.44 | 16.6 |

A steady state flux value

TABLE V

Effect of Miglyol ® 840 on Penetration of Atenolol Across Hairless Mouse Skin

| Solvent System | Drug Conc. % | Flux Value ($\mu$g/cm$^2$/h) | Lag Time (h) |
|---|---|---|---|
| PG | 4 | 38.9 | 22.4 |
| DPH:PG 50:50 w/w | 4 | 148.7 ± 8.76 | 9.1 ± 2.2 |
| Miglyol ® 840:ETOH 80:20 w/w | 1 | 358.01 ± 29 | 0.5 ± 0.16 |

A steady state flux value

TABLE VI

Effect of EtOH, Miglyol ® 840, and EtOH:Miglyol Binary Solvent System on the Permeation of Various Compounds Across Hairless Mouse Skin

| Formulation[a] | Avg. Flux[b] $\mu$g/cm$^2$/h | Enh. F Mix/EtOH | Enh. F Mix/Mig |
|---|---|---|---|
| A. Atenolol | | | |
| EtOH | 50.52 | — | — |
| Mig | 53.73 | — | — |
| EtOH:Mig 20:80 | 262.51 | 5.20 | 4.89 |
| B. Diltiazem | | | |
| EtOH | 13.39 | — | — |
| Mig | 38.93 | — | — |
| EtOH:Mig 20:80 | 59.17 | 4.42 | 1.52 |
| EtOH:Mig | | | |
| 0:100 | 38.93 | | |
| 10:90 | 39.50 | | |
| 20:80 | 59.17 | | |
| 30:70 | 120.10 | | |
| C. Hydrocortisone | | | |
| EtOH | 0.64 | — | — |
| Mig | 1.49 | — | — |
| EtOH:Mig 20:80 | 10.24 | 16.00 | 6.87 |
| D. Tazifylline | | | |
| EtOH | 6.63 | — | — |
| Mig | 30.71 | — | — |
| EtOH:Mig 20:80 | 250.56 | 37.79 | 8.16 |
| E. THA | | | |
| EtOH | 558.91 | — | — |
| Mig | 155.49 | — | — |
| EtOH:Mig 20:80 | 1476.67 | 2.64 | 9.50 |
| F. Verapamil | | | |
| EtOH | 4.80 | — | — |
| Mig | 22.07 | — | — |
| EtOH:Mig 20:80 | 22.85 | 4.76 | 1.04 |

[a]The formulations used in this study were saturated with the corresponding drug except for verapamil.
[b]Calculated by averaging the flux values obained at each sampling time within a 24-hour time period.

A two-ply composite laminate provides an ideal carrier for transdermal delivery of a drug, especially in situations that require large amounts of drug, such as 10 mg per application per day.

Generally the two-ply composite laminate comprises one layer which contains a drug dissolved in propylene glycol dispersed in a mixture of silicone and another layer containing a drug dissolved in Miglyol ®:ethanol (about 80:20) spread on a microporous slab.

The carrier is composed of a silicone elastomer [A] and a macroporous polyethylene slab [B]. The active ingredient may be any desired drug such as a cognition activator, for example, THA or other amine-like drugs that could interfere with the curing process of the silastic fluids by design, forming a free-flowing silicone adhesive matrix for delivery of drugs across a membrane such as skin.

The solvents are mixtures of propylene glycol, mono- or polyhydric alcohols, and propylene glycol dicaprylate/dicaprate.

Preferred ranges of THA in the carrier are: active ingredient, the drug, 10-15% weight-by-weight; propylene glycol 1-5% weight-by-weight and the more preferred is 2-3%; propylene glycol dicaprylate/dicaprate 30-70% weight-by-weight and the more preferred is 45-55%; ethyl alcohol 8-18% and the more preferred is 10-12%.

Preferred ranges for any of the amine-like drugs used in the carrier are 1-20% weight-by-weight of the active ingredient, preferably 4-15% weight-by-weight; propylene glycol 1-5% weight-by-weight, preferably 2-3% weight-by-weight; Miglyol ® 840 5-70%. weight-by-weight, preferably 55-65% weight-by-weight.

Preferred ranges for the steroids are as usually prescribed by one skilled in the art.

One example of a two-ply composite laminate was prepared as described below.

EXAMPLE 1

The silicone elastomer, [A], was prepared by mixing 100 mg of the drug, tacrine, with 1.9 ml of propylene glycol in 8.0 g of silicone fluids (Dow Corning, Midland, Mich.) consisting of Silicone MDX4-4210 10 parts, Silicone MDX4-4210 Curing Agent 1 part and Silicone Fluid 360, 20 cs 16 parts The above mixture was cast onto a hot plate (160° C.) to form a 60–65 cm² 1/16" thick partially cured elastomer. The macroporous polyethylene slab, [B], was prepared by dissolving 2.0 g of drug in a binary solvent mixture made of 20 parts 95% ethanol and 80 parts propylene glycol dicaprylate/dicaprate (Miglyol ® 840, Dynamit Nobel) with mild heating and agitation. The solution was then irrigated into a macroporous PE slab (hydrophobic Interflo ®, 1/16" thick, 35 μm pore size, F/N 35-163-4, Chromex Chemical). After laminating [B] onto [A] at 160° C. for 1.5 minutes, the resultant composite laminate was die cut into smaller discs, each containing 55 mg of the drug within a surface area of 2.8 cm².

The laminate can be cut into any desired size. The resulting disc or patch or matrix can contain from about 5 to about 200 mg of a drug within a surface area of from about 1 to about 50 cm².

We claim:

1. A transmembranally administerable composition with enhanced penetration comprising:
   (a) about 0.1% to about 8% of a therapeutically active medicament selected from the group consisting of diphenhydramine, tetrahydroaminoacridine, atenolol, tazifylline, 2-methoxy-4-[2-(5-methyl-1H-pyrazol-3-yl)ethenyl]phenol, diltiazem, verapamil, estradiol, progesterone, a mixture of estradiol and progesterone and hydrocortisone,
   (b) about 0% to about 99.8% of solvent, and
   (c) about 0% to about 15% of silicone dioxide gelling agent.

2. A composition according to claim 1 comprising:
   (a) about 0.2% to about 8% of a therapeutically active medicament,
   (b) about 0.1% to about 80% of a propylene glycol di-ester of caprylic and capric acids from coconut oil and alcohol, and
   (c) about 0.5% to about 12% of gelling agent.

3. A composition according to claim 1 comprising:
   (a) about 0.2% to about 8% of a therapeutically active medicament, and
   (b) about 0.1% to about 80% of Miglyol ® 840 and alcohol.

4. A composition of claim 1 wherein the therapeutically active medicament is selected from the group consisting of diphenhydramine, tetrahydroaminoacridine, atenolol, tazifylline, 2-methoxy-4-[2-(5-methyl-1H-pyrazol-3-yl)ethenyl]phenol or a pharmaceutically acceptable salt thereof.

5. A composition of claim 1 wherein the therapeutically active medicament is tetrahydroaminoacridine.

6. A composition of claim 1 wherein the therapeutically active medicament is hydrocortisone.

7. A composition of claim 1 wherein the therapeutically active medicament is a sex hormone selected from the group consisting of: estrogens, progestins, and mixtures thereof.

8. A composition of claim 1 wherein the therapeutically active medicament is diphenhydramine.

9. A composition according to claim 1 wherein the Miglyol ® 840 and alcohol are in a ratio of from about 10% to about 90% to about 90% to about 10%.

10. A composition according to claim 9 wherein the alcohol is ethanol.

11. A composition according to claim 10 wherein the ratio is about 80% Miglyol ® 840 to about 20% ethanol.

12. A transmembranally administrable composition comprising:
   (a) a medicament in a therapeutically effective amount and
   (b) a propylene glycol di-ester of caprylic and capric acids from coconut oil and an alcohol in a penetration enhancing effective amount.

13. A transmembranally administrable composition with enhanced penetration comprising
   (a) a therapeutically effective amount of tetrahydroaminoacridine, and
   (b) a penetration enhancing amount of a propylene glycol di-ester of caprylic and capric acids from coconut oil and ethanol.

14. A method of administering a bioaffecting agent comprising contacting a composition of claim 1 with a living membrane.

15. A two-poly composite laminate useful for transmembranal administration comprising, [A], a silicone elastomer, and [B], a macroporous polyethylene slab containing a drug selected from the group consisting of diphenhydramine, tetrahydroaminoacridine, atenolol, tazifylline, 2-methoxy-4-[2-(5-methyl-1H-pyrazol-3-yl)ethenyl]phenol, diltiazem, verapamil, estradiol, progesterone, a mixture of estradiol and progesterone and hydrocortisone dissolved in a binary solvent mixture of ethanol and a propylene glycol diester of caprylic and capric acids from coconut oil.

16. A laminate according to claim 15 wherein the medicament is tetrahydroaminoacridine.

17. A laminate according to claim 15 wherein the medicament is diphenhydramine.

18. A laminate according to claim 15 wherein the medicament is hydrocortisone.

19. A laminate according to claim 15 wherein the medicament is a sex hormone selected from the group consisting of: estrogens, progestins, and mixtures thereof.

20. A laminate according to claim 15 wherein the silicone elastomer [A] comprises a mixture of drug and propylene glycol in silicone fluids.

21. A process for preparing a laminate according to claim 15 which comprises:
   (a) mixing a drug with propylene glycol in silicone fluids,
   (b) casting the mixture onto a hot plate to form a partially cured elastomer [A],
   (c) dissolving a drug in a binary solvent mixture of ethanol and a propylene glycol de-ester of caprylic and capric acids from coconut oil,
   (d) irrigating the solution from (c) above into a macroporous polyethylene slab forming [B], and
   (e) laminating [B] onto [A] to produce the desired laminate and cutting into discs of desired size.

22. A disc comprising a two-poly laminate useful for transmembranal administration comprising [A], a silicone elastomer, and [B], a macroporous polyethylene slab containing a drug selected from the group consisting of diphenhydramine, tetrahydroaminoacridine, atenolol, tazifylline, 2-methoxy-4-[2-(5-methyl-1H-pyrazol-3-yl)ethenyl]phenol, diltiazem, verapamil, estradiol, progesterone, a mixture of estradiol and progesterone and hydrocortisone dissolved in a binary solvent mixture of ethanol and a propylene glycol di-ester of caprylic and capric acids from coconut oil cut into discs having a surface area of from about 1 to about 50 $cm^2$ containing from about 5 to about 200 mg of a drug.

23. A disc according to claim 22 containing from 54–56 mg of a drug within a surface area of 2.8 $cm^2$.

* * * * *

UNITED STATES PATENT AND TRADEMARK OFFICE
CERTIFICATE OF CORRECTION

PATENT NO. : 5,019,395
DATED : May 28, 1991
INVENTOR(S) : Majid Mahjour, et al

It is certified that error appears in the above-indentified patent and that said Letters Patent is hereby corrected as shown below:

Column 9, line 53, "Miglyol® 840" should read --a propylene glycol di-ester of caprylic and capric acids from coconut oil--.

Column 10, line 4, "Miglyol® 840" should read --a propylene glycol di-ester of caprylic and capric acids from coconut oil--.

Column 10, line 9, "Miglyol® 840" should read --a propylene glycol di-ester of caprylic and capric acids from coconut oil--.

Signed and Sealed this

Tenth Day of January, 1995

Attest:

BRUCE LEHMAN

Attesting Officer     Commissioner of Patents and Trademarks